(12) United States Patent
Aylsworth et al.

(10) Patent No.: US 7,213,594 B2
(45) Date of Patent: May 8, 2007

(54) METHOD AND SYSTEM TO DETERMINE NASAL RESISTANCE TO AIRFLOW

(75) Inventors: Alonzo C. Aylsworth, Wildwood, MO (US); Lawrence C. Spector, Austin, TX (US); Mark E. Scott, Houston, TX (US)

(73) Assignee: Acoba, L.L.C., Chesterfield, MO (US)

( * ) Notice: Subject to any disclaimer, the term of this patent is extended or adjusted under 35 U.S.C. 154(b) by 426 days.

(21) Appl. No.: 10/850,496

(22) Filed: May 20, 2004

(65) Prior Publication Data

US 2005/0257788 A1 Nov. 24, 2005

(51) Int. Cl.
*A61M 16/00* (2006.01)
*A62B 7/00* (2006.01)

(52) U.S. Cl. .............................. 128/204.23; 128/205.23

(58) Field of Classification Search ........... 128/205.23, 128/204.23
See application file for complete search history.

(56) References Cited

U.S. PATENT DOCUMENTS

| | | | | |
|---|---|---|---|---|
| 4,054,133 | A | | 10/1977 | Myers |
| 5,042,478 | A | * | 8/1991 | Kopala et al. ......... 128/207.18 |
| 5,046,491 | A | * | 9/1991 | Derrick ................. 128/200.24 |
| 5,069,222 | A | * | 12/1991 | McDonald, Jr. ............ 600/537 |
| 5,704,345 | A | | 1/1998 | Berthon-Jones |
| 6,142,950 | A | * | 11/2000 | Allen et al. ................. 600/529 |
| 6,155,986 | A | | 12/2000 | Brydon et al. |
| 6,165,133 | A | * | 12/2000 | Rapoport et al. ........... 600/529 |
| 6,183,423 | B1 | | 2/2001 | Gaumond et al. |
| 6,213,955 | B1 | * | 4/2001 | Karakasoglu et al. ....... 600/529 |
| 6,332,463 | B1 | * | 12/2001 | Farrugia et al. ....... 128/204.18 |
| 6,484,719 | B1 | * | 11/2002 | Berthon-Jones ........ 128/204.23 |
| 6,536,432 | B2 | * | 3/2003 | Truschel ................ 128/205.23 |
| 6,565,517 | B1 | * | 5/2003 | Rasmussen ................. 600/529 |
| 6,644,311 | B1 | | 11/2003 | Truitt et al. |
| 6,938,619 | B1 | * | 9/2005 | Hickle .................... 128/207.18 |
| 7,114,497 | B2 | * | 10/2006 | Aylsworth et al. ..... 128/204.18 |
| 2003/0140924 | A1 | | 7/2003 | Aylsworth et al. |
| 2005/0020932 | A1 | * | 1/2005 | Haberland et al. .......... 600/538 |

OTHER PUBLICATIONS

Malcolm Kohler et al., Non-Invasive, side-selective nasal airflow monitorting, 2005, Physiological Measurement vol. 26 pp. 69-82, www.iop.org/EJ/abstract/0967-3334/26/1/007.*
RHINOMANOMETER [online], Retrieved from the Internet: <URL: http://www.nagelnetwork.com/rhino.htm>.

* cited by examiner

*Primary Examiner*—Patricia Bianco
*Assistant Examiner*—Kiandra C Lewis
(74) *Attorney, Agent, or Firm*—Mark E. Scott; Conley Rose, P.C.

(57) ABSTRACT

A method and related system to determine nasal resistance to airflow. Some of the exemplary embodiments may be a method comprising measuring an attribute of airflow through a first naris of a patient without blocking a second naris of the patient, measuring an attribute of airflow through the second naris of the patient without blocking the first naris, and determining a value indicative of nasal resistance to airflow based on the attributes measured.

14 Claims, 4 Drawing Sheets

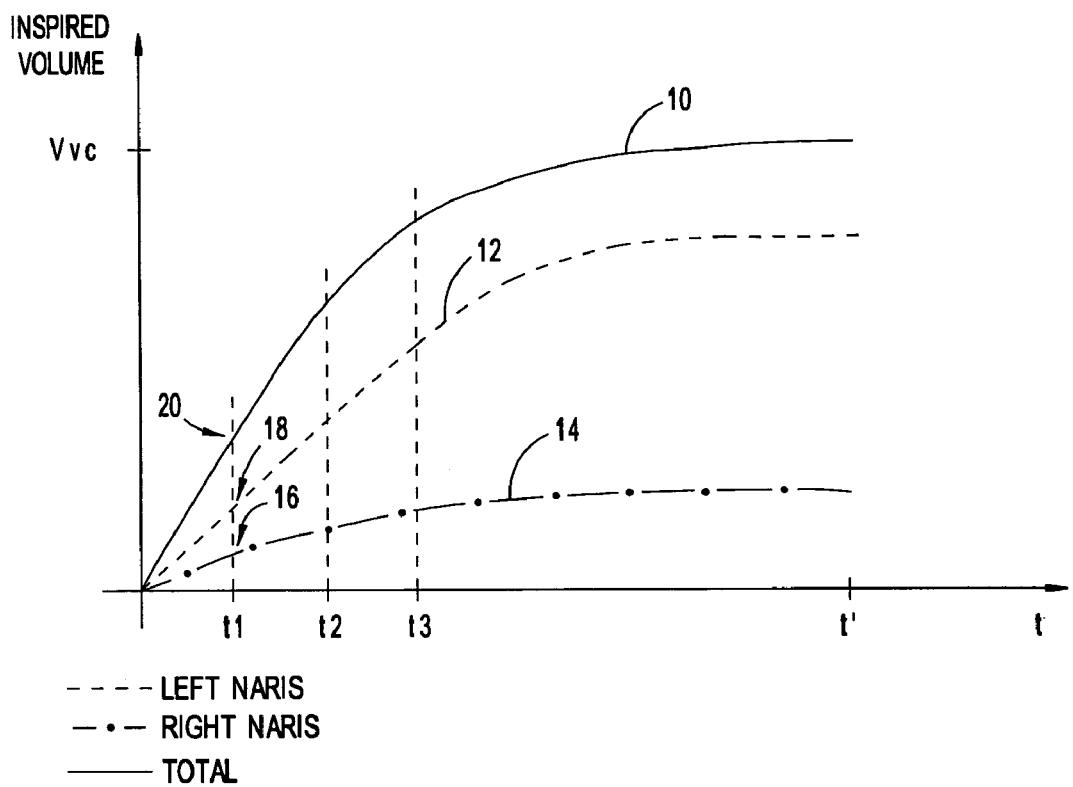
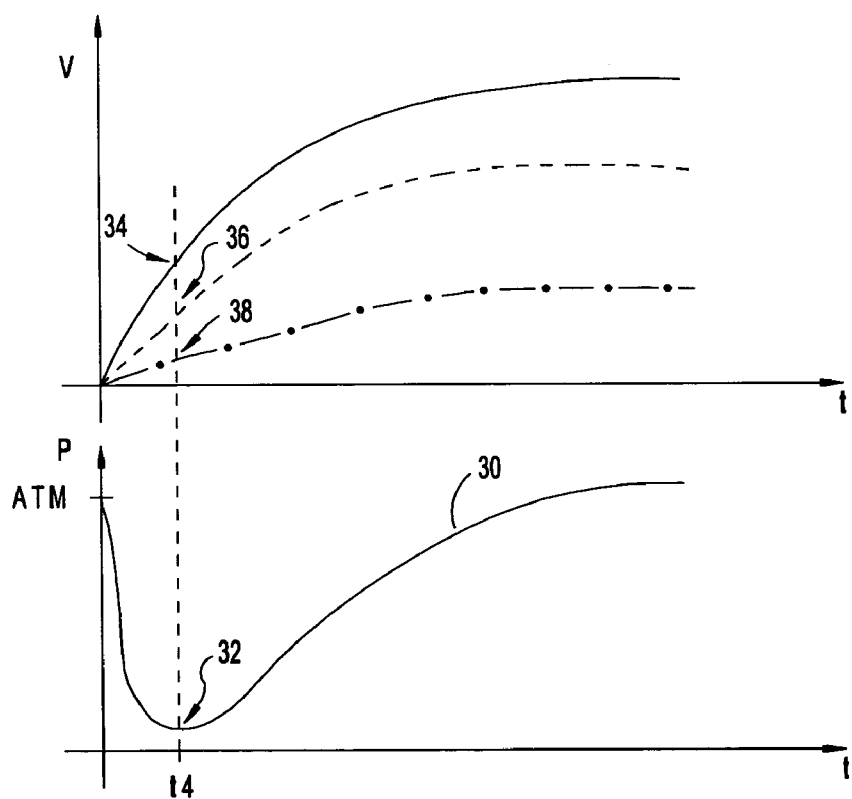
FIG 2

METHOD AND SYSTEM TO DETERMINE NASAL RESISTANCE TO AIRFLOW

CROSS-REFERENCE TO RELATED APPLICATIONS

None.

STATEMENT REGARDING FEDERALLY SPONSORED RESEARCH OR DEVELOPMENT

Not applicable.

BACKGROUND OF THE INVENTION

1. Field of the Invention

Embodiments of the invention are directed to methods and systems of calculating the resistance to airflow of the nostrils of a patient, also known as nasal resistance.

2. Background of the Invention

Knowing the nasal resistance of a person's nostrils or nares may be useful in predicting and diagnosing many ailments associated with the nose and nasopharynx. For example, knowing the nasal resistance may be useful in quantifying a degree of congestion experienced by a patient. Further, knowing the nasal resistance may be useful in determining the degree or extent of a physical abnormality, such as a deviated septum.

One related art method that may be used to determine nasal resistance is known as rhinomanography. Rhinomanography may be a technique of recording nasal pressure of an intentionally blocked naris, and simultaneously recording flow through an unblocked naris. Rhinomanography in accordance with the related art may be a multi-step process. In particular, a first naris may be blocked by a pressure gauge or meter. Thereafter, the entire nose and mouth of the patient may be covered and airflow through the unblocked naris measured in relation to the pressure developed in the blocked naris. Thereafter, the blocked and unblocked naris may be switched and a second set of data collected regarding airflow through the second naris with respect to nasal pressure.

As can be appreciated from the description above, a rhinomanographic test may be a complicated process. Airflow measured through each naris is with the other naris blocked, and therefore nasal resistance calculated is not with respect to normal breathing patterns. Further, the act of plugging a naris, so as to read nasal pressure, may cause swelling of the nasal tissue which may in turn affect airflow through that naris and skew the calculated nasal resistance.

SUMMARY OF SOME OF THE EMBODIMENTS

The problems noted above are solved in large part by a method and related system to determine nasal resistance to airflow. Some of the exemplary embodiments may be a method comprising measuring an attribute of airflow through a first naris of a patient without blocking a second naris of the patient, measuring an attribute of airflow through the second naris of the patient without blocking the first naris, and determining a value indicative of nasal resistance to airflow based on the attributes measured.

Other exemplary embodiments may be a method comprising measuring airflow through a first naris of a patient, measuring a pressure within the patient's mouth substantially simultaneously with measuring airflow through the first naris, and determining a value indicative of nasal resistance using the pressure and measured airflow.

Still other exemplary embodiments may be a method comprising determining an oral airflow rate for a patient taking an oral only breath to substantially vital capacity, determining an airflow rate through a first naris for a patient taking a nasal only breath to substantially vital capacity, and calculating a value indicative of nasal resistance using the oral airflow rate and the airflow rate through the first naris.

Yet other exemplary embodiments may be a system comprising a processor, a memory device coupled to the processor, a first sensor electrically coupled to the processor, and a second sensor electrically coupled to the processor. The first sensor fluidly couples to a first sensing tube in operational relationship to a first naris of a patient, the second sensor fluidly couples to a second sensing tube in operational relationship to a second naris of the patient, and the first and second sensors each generate an electrical signal proportional to airflow through the first and second naris respectively. The processor, executing a program stored on the memory, determines a value indicative of nasal resistance using the electrical signals proportional to airflow.

The disclosed devices and methods comprise a combination of features and advantages which enable it to overcome the deficiencies of the prior art devices. The various characteristics described above, as well as other features, will be readily apparent to those skilled in the art upon reading the following detailed description, and by referring to the accompanying drawings.

BRIEF DESCRIPTION OF THE DRAWINGS

For a detailed description of the preferred embodiments of the invention, reference will now be made to the accompanying drawings in which:

FIG. 1 illustrates a graph of inspired volume as a function of time for an exemplary inspiration to vital capacity;

FIG. 2 illustrates reproduces the exemplary graph of inspired volume of FIG. 1, and also shows an exemplary graph of an oral pressure reading for a corresponding period of time;

NOTATION AND NOMENCLATURE

Figure 3:
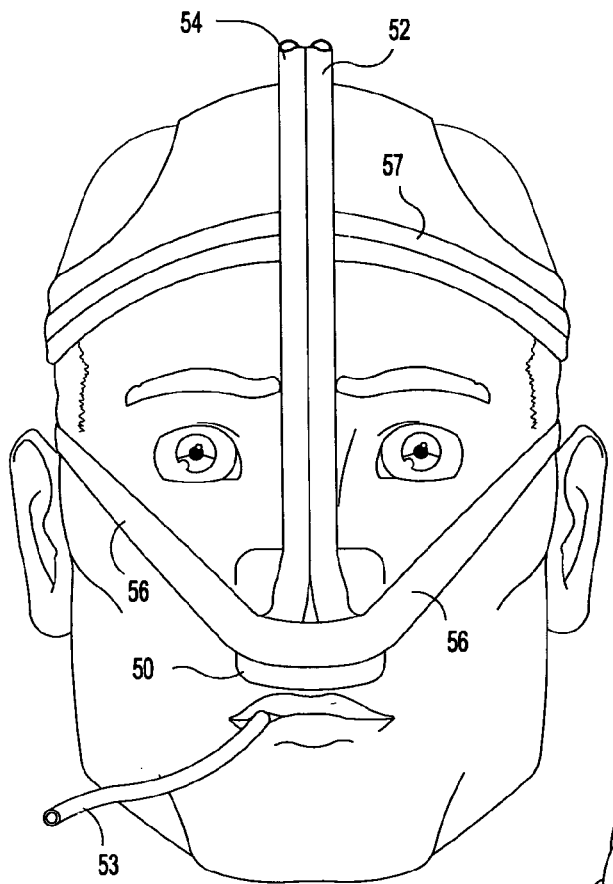
FIG. 3 illustrates a respiratory mask which may be use in accordance with embodiments of the invention.

Certain terms are used throughout the following description and claims to refer to particular system components. This document does not intend to distinguish between components that differ in name but not function.

In the following discussion and in the claims, the terms "including" and "comprising" are used in an open-ended fashion, and thus should be interpreted to mean "including, but not limited to . . . ". Also, the term "couple" or "couples" is intended to mean either an indirect or direct connection. Thus, if a first device couples to a second device, that connection may be through a direct connection, or through an indirect connection via other devices and connections.

DETAILED DESCRIPTION OF THE PREFERRED EMBODIMENTS

The various embodiments of the invention are directed to determining a value proportional to, or indicative of, the nasal resistance of a patient. In accordance with embodiments of the invention, the value indicative of nasal resistance is determined by individually measuring airflow through each naris during an inspiration, possibly to full vital capacity. In this specification, and in the claims, the term "vital capacity" shall mean the volume of air required to substantially fill a patient's lungs. In some embodiments, the time required to reach vital capacity is also measured. The inhalation to vital capacity is preferably at a maximum effort (maximum inspired air velocity), but similar results may be achieved at less than maximum effort and/or at less than vital capacity of the lungs.

FIG. 1 illustrates a graph of inspired volume as a function of time for an exemplary inspiration to vital capacity. In particular, solid line 10 represents the inspired volume as a function of time. As illustrated, inspired volume initially rises quickly, and then exponentially approaches the vital capacity ($V_{vc}$). In some embodiments, the amount of time it takes the patient to reach vital capacity, T' in FIG. 1, is the value indicative of nasal resistance. Using the time T' to reach vital capacity at maximum effort as a value indicative of nasal resistance works best in situations where the patient is measured on several occasions (e.g., over the course of hours, days or weeks) or otherwise has a baseline inspiration T' measured before the onset of nasal congestion or distress.

Referring still to FIG. 1, in a nasal only inhalation the total inspired volume (line 10) is made up of contributions from both the left naris (line 12) and the right naris (line 14). For a patient having no nasal congestion, and no physical abnormality blocking one of the nares, the inspired volume as between each naris would be substantially the same. FIG. 1, however, illustrates a situation where one naris has substantially lower airflow (and therefore greater nasal resistance) than a second naris. In accordance with alternative embodiments of the invention, the value indicative of nasal resistance may be the airflow into a naris in relation to the combination or total airflow. For example, and still referring to FIG. 1, the total volume indicated at point 16 for the right naris, divided by the time T1, gives an average airflow rate to that point for the right naris. Likewise, the volume indicated at point 18 for the left naris divided by the time T1 gives an average airflow rate for the left naris. Finally, the volume indicated at point 20 for the combined left and right nares, divided by the time T1, gives an average airflow rate. The average airflow rate of the left naris at time T1 divided by the total average airflow rate at time T1 gives a value indicative of nasal resistance of the left naris. Likewise, the average airflow rate of the right naris at time T1 divided by the total average airflow rate at time T1 gives a value indicative of the nasal resistance of the right naris. Using volumes recorded at time T1 to calculate the value indicative of nasal resistance is merely exemplary, and in accordance with these embodiments may take place using the volumes recorded at any time, such as T2, T3, and/or T'. In accordance with alternative embodiments of the invention, instantaneous airflow rate may be used, possibly as determined by a flow sensor in a measurement device, to calculate the values indicative of nasal resistance rather than average airflow.

In accordance with yet further alternative embodiments, the value indicative of nasal resistance may be the volume inspired through a naris divided by the total volume. Referring still to FIG. 1, and time T1, determining the value of nasal resistance for the exemplary left naris in accordance with these embodiments may involve dividing the volume at time T1 for the left naris (point 18) by the total volume (point 20). A similar calculation may be made for the right naris.

The embodiments described to this point have relied on individually measuring airflow through each naris during an inspiration, and determining a value indicative of nasal resistance based on the measured airflows. Alternative embodiments of the invention use not only measured airflow, but also a pressure reading. Unlike the rhinomanography which uses the pressure within an artificially blocked naris, pressure readings in accordance with these embodiments of the invention are taken orally during the inspiration. More particularly, the pressure reading is the pressure within the mouth and/or throat during nasal only inspiration. FIG. 2 reproduces the exemplary graph of inspired volume of FIG. 1, and also shows an exemplary graph of an oral pressure reading (line 30) for the same period of time. As illustrated, initially the pressure within the mouth and/or throat is approximately equal to atmospheric pressure (ATM). As the patient attempts to inhale through the nostrils, the pressure within the lungs and throat drops. At a maximum displacement of the patient's diaphragm in early stages of the inhalation, a minimum pressure is achieved (point 32). As lungs begin to fill with air, the pressure approaches atmospheric again, and thus the graph of pressure as a fraction of time has a shape similar to the volume curves of FIG. 1. Determining a value indicative of nasal resistance in these embodiments may involve application of the following equation:

$$NR = \frac{|\Delta P|}{FR} \qquad (1)$$

where NR is the nasal resistance, $\Delta P$ is the measured difference between atmospheric pressure and the pressure within the mouth and/or throat, and FR is the airflow rate. In cases where a total nasal resistance is desired, the airflow rate FR is the total average or instantaneous airflow, for example at point 34. If nasal resistance of a single naris is desired, the term FR may be the instantaneous and/or average airflow of the left naris (point 36) or the right naris (point 38). Nasal resistance calculation in these embodiments is preferably made using values of the various parameters at the minimum pressure developed during the inspiration; however, the nasal resistance calculation may be based on values of the various parameters at any time during the inspiration.

FIG. 3 illustrates a respiratory mask which may be used in combination with other hardware (discussed below) to measure narial airflow. In particular, the mask may comprise a nose portion 50 which fluidly and sealingly couples sensing tube 52 to a first naris (in this case the left naris), and fluidly and sealingly couples sensing tube 54 to a second naris (in this case the right naris). The nose portion 50 may be held in place by a strap 56. Strap 57 may also hold the sensing tubes 52 and 54 in the relative position shown, extending over the forehead. Each sensing tube 52, 54 preferably individually seals to its respective naris by a sealing surface contacting an outer portion of each naris. In alternative embodiments, the nose portion may comprise tubular members which extend some distance into each naris, thus forming a seal with the internal portions of the naris. However, sealing against the internal portion of the naris may act as an artificial stent, which may affect nasal resistance readings, and therefore the distance the sensing tubes protrude into the nares should be minimized. In embodiments where oral pressure is measured, sensing tube 53 may be used. Sensing tube 53 may be separate from the mask as shown, or integrated with the mask.

Figure 4:
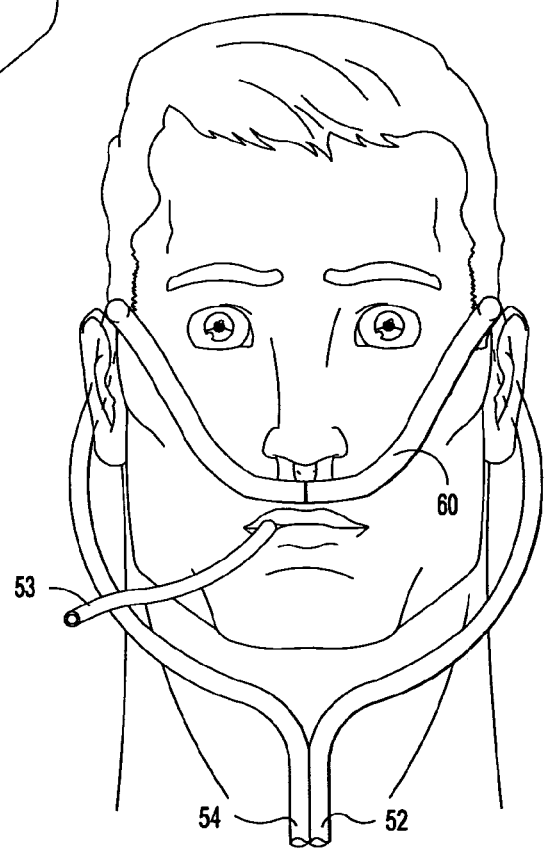
FIG. 4 illustrates use of a nasal cannula in accordance with embodiments of the invention.

Embodiments using a mask such as illustrated in FIG. 3 may measure substantially all the airflow into each naris individually. In order to simplify the testing procedure, and possibly to reduce mask cost and therefore testing costs, some embodiments of the invention may determine a value indicative of nasal resistance using a bifurcated nasal cannula. FIG. 4 illustrates a bifurcated nasal cannula 60 comprising sensing tubes 52 and 54. As one of ordinary skill in the art is aware, a cannula is used for the delivery of oxygen for patient inspiration, and does not seal against the nostrils. However, in accordance with at least some embodiments of the invention, a cannula may be used to measure, at least in part, the airflow inspired by the patient. U.S. Pat. No. 7,066,180, titled "Method and System for Measuring Airflow of Nares," describes in detail measuring the relative airflow between the nares of a patient using a bifurcated nasal cannula, and is incorporated by reference herein as if reproduced in full below.

In embodiments where the full narial airflow is measured, such as by embodiments using the mask illustrated in FIG. 3, having the patient inspire to vital capacity at maximum effort may be accomplished as soon as the mask is in place. However, testing using a bifurcated nasal cannula may require correlating measured airflow to actual airflow prior to determining the value indicative of nasal resistance.

Figure 5:
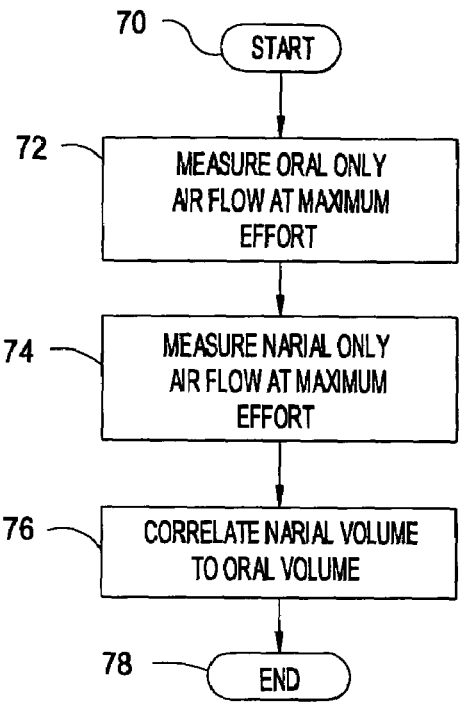
FIG. 5 illustrates a high level flow diagram for determining nasal resistance in accordance with embodiments of the invention.

FIG. 5 illustrates a high level flow diagram for determining nasal resistance in accordance with embodiments of the invention using a bifurcated nasal cannula. The method may start (block 70) and proceed to a measurement of oral only airflow at maximum effort (block 72), such as through sensing tube 53. While maximum effort is preferred, other efforts could be used. During this first step, either the patient does not breathe through the nares, or the nares are blocked. Inasmuch as pinching and/or internally plugging the nares may cause swelling which affects later testing, if physical blocking is needed this is preferably accomplished by sealing a structure to the external surfaces of each naris.

Measuring the oral airflow provides an indication of vital capacity, and is also used to correlate airflow measurements made with the bifurcated nasal cannula to actual airflow. Thus, next step may be measuring narial only airflow (block 74), possibly at maximum effort. Because only a portion of the total airflow into each naris is sensed by the cannula, the next step may be correlating total narial volume (of step 74) sensed by the cannula to vital capacity of step 72, and the process ends (block 78).

Consider, for purposes of explanation, that vital capacity of a patient's lungs is ten units, and that an oral only inspiration takes two seconds to fill the lungs. Further consider that in a nasal only inspiration taking six seconds to fill the lungs, seven units flow through the left naris, and three units flow through the right naris. Table 1 below illustrates the volumes, times and airflow rates of this exemplary situation.

TABLE 1

|  | Volume (Units) | Time (Seconds) | Airflow Rate (Units/Second) |
|---|---|---|---|
| Oral | 10 | 2 | 5 |
| Narial | 10 | 6 | 1.67 |
| Left Naris | 7 | 6 | 1.17 |
| Right Naris | 3 | 6 | 0.5 |

As illustrated in Table 1, the average oral airflow rate (total volume divided by time) is 5 units per second in the exemplary situation. For the left naris, the airflow rate is 1.17 units per second, and for the right naris the airflow rate is 0.5 units per second. Thus, the total narial airflow rate is 1.67 units per second in this exemplary situation.

Figure 6:
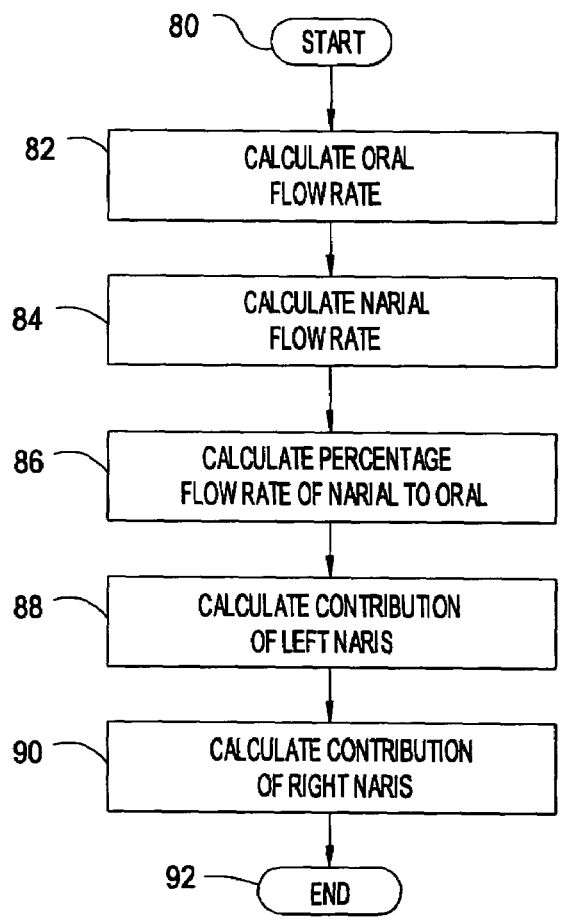
FIG. 6 illustrates calculating nasal resistance in accordance with at least some embodiments of the invention.

In some embodiments, calculating the value indicative of nasal resistance is a function of the oral airflow rate, the total narial airflow rate, and the airflow rate of each of the left naris and right naris considered individually. FIG. 6 is a flow diagram that illustrates calculating nasal resistance in accordance with these embodiments of the invention, and will be discussed in conjunction with the exemplary set of numbers of Table 1 to illustrate the calculations. However, it should be understood that the values of Table 1 are merely exemplary and the specific ranges and times should not be construed as a limitation of the applicability of the invention. In particular, the process may start (block 80) and proceed to calculating airflow rate for an oral only test (block 82). Using the exemplary data of Table 1, the oral airflow rate may be calculated by dividing the total volume of ten units by the time to reach vital capacity of two seconds to arrive at an airflow rate of five units per second. In alternative embodiment of the invention, the device through which the patient breathes to determine lung volume may also provide an airflow rate indication. Thus, no calculation may be required, or it may be that the rates over the course of the inspiration may have to be averaged.

After calculating the oral airflow rate, the next step may be calculating the narial only airflow rate (block 84). That is, after correlating the measured narial volume to the oral volume (for cannula-based determinations), the total narial volume is divided by the time to achieve the volume, preferably at or near vital capacity. In the exemplary data of Table 1, the total narial volume of 10 units is therefore divided by the total time to inhale the 10 units of six seconds to arrive at a total narial airflow rate of 1.67 units per second. The next step in the process may be calculating a percentage of the narial airflow rate in relation to the oral airflow rate (block 86). In the exemplary data of Table 1, this percentage may be calculated by dividing the narial airflow rate of 1.67 units per second by the oral flow rate of 5 units per second, and multiplying by 100 to arrive at 33.4 percent. After calculating the percent narial airflow of the oral airflow, the next step in the process may be calculating the contribution of the left naris to the calculated percentage (block 88). In the exemplary data of Table 1, the left naris represents seven units of the total 10 units, and 0.7 multiplied the percent narial of oral airflow of 33 percent equals 23 percent. Likewise, the contribution of the right naris may be calculated (block 90). In the exemplary data of Table 1, the right naris represents three units of a total of 10 units, and therefore the contribution may be 0.3 multiplied by 33 percent or 10 percent In alternative embodiments, the contribution of the individual naris may be calculated directly as a percentage of the individual naris airflow rate to the total oral airflow rate. in the exemplary data of Table 1 then, the airflow rate of the left naris of 1.17 units per second may be divided by the oral airflow rate of 5 units per second, and multiply by 100 to arrive directly at the 23 percent. Likewise, the airflow rate of the right naris of 0.5 units per second may be divided by the oral airflow rate of 5 units per second and multiplied by 100 to arrive at 10 percent. Thereafter, the process ends (block 92).

Figure 7:
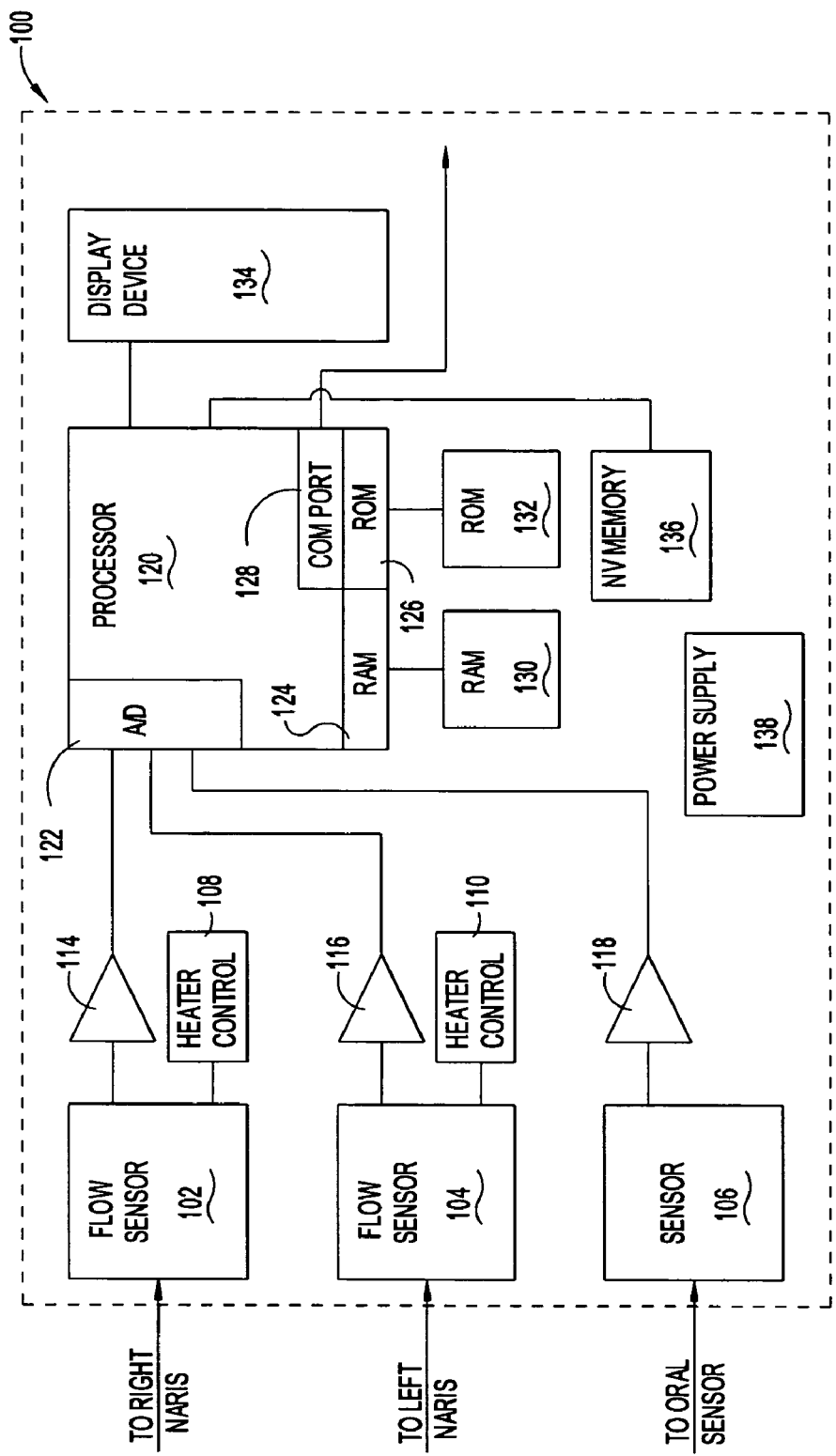
FIG. 7 illustrates a nasal function test device constructed in accordance with embodiments of the invention.

FIG. 7 illustrates a nasal function test device 100 constructed in accordance with at least some embodiments of the invention. The nasal function test device 100 may comprise a flow sensor 102 adapted to fluidly couple to a sensing tube, such as sensing tube 52 FIG. 3 or 4. The nasal function test device 100 may also comprise a second flow sensor 104 adapted to fluidly couple to a sensing tube, such as sensing tube 54 of FIG. 3 or 4. The nasal function test device 100 may also optionally comprise a sensor 106 adapted to fluidly couple to a sensing tube, such a sensing tube 53 of FIG. 3 or 4. Sensor 106 may be a flow sensor for embodiments that use oral volume to correlate cannula-based measurements, and may be a pressure sensor in embodiments that use the pressure in the mouth and/or throat to calculate values indicative of nasal resistance. In accordance with at least some embodiments of the invention, the flow sensors 102 and 104 (and possibly sensor 106) may be mass flow sensors available from Microswitch (a division of Honeywell Corp.) having part No. AWM92100V. However, other sensors, such as other brands of flow sensors as well as pressure sensors, may be equivalently used. The preferred flow sensors may operate on the principle of a heated element within the air stream in the flow sensor that experiences different cooling effects depending on airflow. In embodiments using flow sensors based on heated elements, heater control circuit 108 and 110 may be used. Airflow sensors of differing technology may not require the heater control circuits. In situations where sensor 106 is a pressure sensor, a Motorola MPXV5004DP pressure transducer may be used.

The nasal function test device 100 of FIG. 7 may also comprise amplifiers 114, 116 and 118 coupled to an output signal of each of the sensors 102, 104 and 106 respectively. The purpose of the amplifiers 114, 116 and 118 may be to amplify the output signals propagating from each of the sensors. Depending on the type of sensors used, the amplifiers 114, 116 and 118 may not be needed. In accordance with embodiments of the invention, each flow sensor 102 and 104 may produce an output signal that has an attribute that changes proportional to the amount of airflow through the flow sensor. Sensor 106 has an output signal that has an attribute that changes proportional to airflow and/or sensed pressure. Any attribute of an electrical signal may be used, such as frequency, phase, current flow, or possibly a message based system where information may be coded in message packets. In the preferred embodiments each sensor (and related amplifier if used) produces an output signal whose voltage is proportional to the measured values. In order that the output signals of the sensors 102, 104 and 106 may be read and analyzed, each of the sensors may couple to a processor 120, possibly through an analog-to-digital (A/D) converter 122.

In the illustration of FIG. 7, processor 120 is shown to have an on-board A/D converter 122, on-board random access memory (RAM) 124, on-board read-only memory (ROM) 126, as well as on-board serial communication ability, as illustrated by communication port 128. In embodiments where these devices (and possibly others) are integral with the processor, the processor may be any of a number of commercially available microcontrollers. Thus, the processor 120 could be a microcontroller produced by Cypress Micro Systems having a part No. CY8C26643. Random access memory, such as RAM 124, may provide a working area for the processor to temporarily store data, and from which programs may be executed. Read-only memory, such as ROM 126, may store programs, such as an operating system, to be executed on the processor 120. ROM may also store user-supplied programs which perform specific tasks. Although microcontrollers may have on-board RAM and ROM, in some embodiments of the invention additional RAM 130 and/or additional ROM 132 may be coupled to the processor 120. In accordance with embodiments of the invention, ROM 126 may store programs specifically designed to calculate the values indicative of nasal resistance discussed above. In particular, when executed, the programs may periodically read the signal levels from the sensors 102, 104 and 106. Preferably, the measuring or reading of the measured signals take place substantially simultaneously. "Substantially simultaneously" shall mean that the signals produced by the sensors may be read within the same period of time. This, as opposed to, for example, reading the response of a first naris during a first respiratory cycle, the reading the response of a second naris during a different respiratory cycle. Thus, while a single microcontroller or single processor nasal function test device may only be able to read samples one at a time, substantially simultaneously may mean that output signals of multiple sensors may be sample multiple times during a single inspiration.

In alternative embodiments of the invention, the functionality of the microcontroller may be implemented using individual components, such as an individual microprocessor, individual RAM, individual ROM, and an individual A/D converter.

Still referring to FIG. 7, the nasal function test device 100 may further comprise a indicator or display device coupled to the processor 120. While the display device may take many forms, in accordance with embodiments of the invention the display device 134 may comprise a liquid crystal display (LCD), such as an LCD display Part No. TM320240DFG1 available from TIAN-MA Microelectronics Company. Depending on the type of display device 134 used, the processor 120 may communicate information to the user of the nasal function test device 100. In some embodiments, the communication may be by placing alphanumeric characters on the display device 134. In alternative embodiments, the display device 134 may be capable of graphically imparting information to the user of the nasal function test device 100, such as by displaying a graph of the measured flows and/or pressures as a function of time, along with the calculated values indicative of nasal resistance.

The nasal function test device 100 as illustrated in FIG. 7 may also comprise a non-volatile memory (NV memory) 136 coupled to the processor 120. In accordance with at least some embodiments of the invention, the nasal function test device 100 may have the capability of comparing nasal resistance values of a patient performed at different times. The non-volatile memory 136 could be battery-backed random access memory, some form of electrically erasable, programmable read-only memory (EEPROM), or some other now-existing or after-developed technology. In alternative embodiments, the non-volatile memory 136 may comprise a removable or non-removable disk drive.

The nasal function test device 100 may also comprise a power supply 138. In accordance with at least some embodiments of the invention, the power supply 138 may be capable of taking alternating current (AC) power available at a standard wall outlet and converting it to one or more direct current (DC) voltages for use by the various electronics within the system. In alternative embodiments where the nasal function test device 100 may be portable, the power supply 138 may have the capability of switching between converting the AC wall power to DC, or drawing current from on-board or external batteries, and converting to voltages needed by the devices within the nasal function test device. In yet further embodiments, the power supply 138 may be housed external to the nasal function test device 100.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

What is claimed is:

1. A method comprising:
   measuring an attribute of airflow through a first naris of a patient without blocking a second naris of the patient;
   measuring an attribute of airflow through the second naris of the patient without blocking the first naris;
   measuring an amount of time to inhale a breath having a volume substantially equal to the patient's vital capacity; and
   determining a value indicative of nasal resistance to airflow based on the attributes measured and the amount of time.

2. The method as defined in claim 1 wherein the amount of time to inhale the breath having a volume substantially equal to the patient's vital capacity is the value indicative of nasal resistance.

3. A method comprising:
   measuring an airflow rate through a first naris of a patient without blocking a second naris; and
   measuring an airflow rate through the second naris of the patient without blocking the first naris; and
   determining a value indicative of nasal resistance by dividing the airflow rate of the first naris by a combined airflow rate of the first naris and the second naris.

4. The method as defined in claim 3 further comprising:
   wherein measuring airflow rate through the first naris further comprises measuring an instantaneous airflow rate through the first naris; and
   wherein measuring airflow rate through the first naris further comprises measuring an instantaneous airflow rate through the second naris;
   wherein determining the value indicative of nasal resistance further comprises dividing the instantaneous airflow rate through the first naris by a combined instantaneous airflow rate through the first naris and the second naris.

5. A method comprising:
   measuring a volume of airflow through a first naris of a patient without blocking a second naris of the patient; and
   measuring a volume of airflow through the second naris of the patient without blocking the first naris; and
   determining a value indicative of nasal resistance to airflow based on the volumes measured by dividing the volume of airflow through the first naris by a combined volume of airflow through the first and second naris.

6. The method as defined in claim 5 further comprising dividing the volume of airflow through the first naris during an inhalation to vital capacity by the combined volume of airflow.

7. The method as defined in claim 5 wherein the measuring is performed substantially simultaneously.

8. The method as defined in claim 5 wherein the measuring is performed during an inhalation.

9. A system comprising:
   a processor;
   a memory device coupled to the processor;
   a first sensor electrically coupled to the processor; and
   a second sensor electrically coupled to the processor;
   wherein the first sensor fluidly couples to a first sensing tubing in operational relationship to a first naris of a patient the second sensor fluidly couples to a second sensing tube in operational relationship to a second naris of the patient, and the first and second sensors measure an attribute of airflow through first naris and second naris respectively;
   wherein the processor determines a value indicative of nasal resistance by one or more selected from the group consisting of: dividing the attributes of airflow through the first naris by a combined attribute of airflow of the first and second naris; and by determining an amount of time it takes a patient to inhale a nasal only breath having a volume substantially egual to the patient's lung capacity.

10. The system as defined in claim 9 wherein the first and second sensing tubes form a bifurcated nasal cannula.

11. The system as defined in claim 9 wherein the first and second sensing tubes are part of a respiratory mask, and wherein the first and second sensing tubes sealingly engage one each to their respective naris.

12. The system as defined in claim 9 wherein first and second sensors are airflow sensors, and wherein the first and second sensors measure at least a portion of the airflow through their respective naris.

13. The system as defined in claim 9 wherein the first and second sensors are pressure sensors, and wherein the first and second sensors measure air pressure within the sensing tubes proportional to airflow through their respective naris.

14. The system as defined in claim 9 further comprising:
   a third sensor electrically coupled to the processor and fluidly coupled to a sensing tube in operational relationship to the mouth of the patient, the third sensor measures one of airflow through the mouth or pressure in the mouth;
   wherein the processor determines a value indicative of nasal resistance value using the attributes of airflow measured by the first and second sensors and the measurement of the third sensor.

* * * * *